United States Patent [19]

Robson et al.

[11] 4,126,684

[45] Nov. 21, 1978

[54] 4-AMINO-3-p-HALOPHENYLBUTYRIC ACIDS AND THEIR DERIVATIVES USED IN THE CONTROL OF NARCOTIC ABUSE

[75] Inventors: Ronald D. Robson, Mendham; Jeffrey K. Saelens, North Brunswick, both of N.J.

[73] Assignee: Ciba-Geigy Corporation, Ardsley, N.Y.

[21] Appl. No.: 748,591

[22] Filed: Dec. 8, 1976

Related U.S. Application Data

[63] Continuation-in-part of Ser. No. 656,996, Feb. 11, 1976, abandoned.

[51] Int. Cl.$^2$ .................. A61K 31/515; A61K 31/195
[52] U.S. Cl. .................................... 424/254; 424/260; 424/263; 424/266; 424/267; 424/309; 424/319; 424/330
[58] Field of Search ................ 424/260, 309, 319, 254

[56] References Cited

U.S. PATENT DOCUMENTS

| | | | |
|---|---|---|---|
| 3,471,548 | 10/1969 | Kererle et al. | 424/319 |
| 3,773,955 | 11/1973 | Pachter et al. | 424/10 |

OTHER PUBLICATIONS

Cutting et al., Br. J. Pharmac., (1975), 54, 171–179.
Physicians Desk Reference, (PDR), 25th Ed., (1971), pp. 1449–1450.
Physicians Desk Reference, (PDR), 26th Ed., (1972), (Isordil with Phenobarbital), pp. 758–759.
Brodie—New Zealand Medical Journal, 22, 157, Aug. 27, 1975.

*Primary Examiner*—Leonard Schenkman
*Attorney, Agent, or Firm*—Theodore O. Groeger

[57] ABSTRACT

4-Amino-3-p-halophenylbutyric acids, acyl derivatives, esters and/or salts thereof reduce addiction liability, particularly that of narcotics, or the withdrawal symptoms observed after interruption of prolonged use of addicting agents, especially of narcotics.

7 Claims, No Drawings

4-AMINO-3-p-HALOPHENYLBUTYRIC ACIDS AND THEIR DERIVATIVES USED IN THE CONTROL OF NARCOTIC ABUSE

CROSS-REFERENCE TO RELATED APPLICATION

This is a continuation-in-part of application Ser. No. 656,996, filed Feb. 11, 1976 (now abandoned).

BACKGROUND OF THE INVENTION

4-Amino-3-p-halophenylbutyric acids and suitable derivatives thereof are disclosed in U.S. Pat. Nos. 3,471,548 and 3,634,428 and one member thereof, i.e. baclofen [4-amino-3-p-chlorophenylbutyric acid or β-(aminomethyl)-p-chlorohydrocinnamic acid respectively], is the active ingredient of the muscle relaxant LIORESAL ®. Moreover, non-spasmolytic doses of baclofen were described in Brit. J. Pharmacol. 54, 171 (1975) as enhancing the analgesic action of morphine. Surprisingly it was found that said 4-amino-3-p-halophenylbutyric acids and derivatives thereof, especially baclofen, do not necessarily enhance the other effects of morphine, in particular the drug seeking behavior and physical dependence liability. They actually depress the symptoms of withdrawal of addicting agents, particularly of narcotics, such as morphine, and reduce the craving for said agents, particularly for morphine administration. Therefore, combinations of addicting agents, e.g. narcotics, especially with said 4-amino-3-p-halophenylbutyric acids, or derivatives thereof, should be administered, in order to prevent future addiction, or to ameliorate the withdrawal symptoms in the addicted.

SUMMARY OF THE INVENTION

The present invention concerns and has for its object the provision of: (1) a pharmaceutical composition comprising: (A) an effective amount of an addicting agent, (B) an effective amount of a 4-amino-3-p-halophenylbutyric acid, a suitable acyl derivative, ester or salt thereof, which neither enhances an analgesic agent, nor impairs muscle coordination and (C) a pharmaceutical excipient, and, (2) a method for reducing either the addiction liability of an addicting agent, or the withdrawal symptoms caused by it, which consists in administering to a mammal in need of said agent, or suffering from withdrawal symptoms caused by the lack of it, enterally or parenterally either a composition according to item one, or (3) a pharmaceutical composition comprising an amount of the compounds according to item (B) which neither enhances an analgesic agent, nor impairs muscle coordination, in conjunction with the excipient according to item (C). Said new compositions and methods are valuable therapeutic regimens, for example in surgery, or in the prevention of abuse of addicting agents, particularly of narcotic abuse, and in the management of the chronically ill.

DESCRIPTION OF THE PREFERRED EMBODIMENTS

The addicting agents most suitable for the compositions claimed herein are preferably narcotics, such as those commonly prescribed for pain and discomfort, e.g. alphaprodine, anileridine, bezitramide, codeine, dihydrocodeine, diphenoxylate, ethylmorphine, fentanyl, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan or thebaine, or their salts.

Also for those narcotics, often illegally abused, a withdrawal-cure may be beneficial in conjunction with said 4-amino-3-p-halophenylbutyric acids or said derivatives thereof. Such narcotics are, for example, acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, codeine methylbromide, codeine-N-oxide, cyprenorphine, desomorphine, dextromoramide, dextrorphan, diampromide, diethylthiambutene, dihydromorphine, dimenoxadol, dimepheptanol, dimethylthiamubutene, dioxaphetyl butyrate, dipipanone, drotebanol, ethylmethylthiambutene, etonitazene, etorphine, etoxeridine, furethidine, heroin, hydromorphinol, hydroxypethidine, ketobemidone, levomoramide, levophenacylmorphan, methyldesorphine, methyldihydromorphine, morpheridine, morphine methylbromide, morphine methylsulfonate, morphine-N-oxide, myrophin, nicocodeine, nicomorphine, noracymethadol, norlevorphanol, normethadone, normorphine, norpipanone, phenadoxone, phenampromide, phenomorphan, phenoperidine, piritramide, pholcodine, proheptazine, properidine, propiram, racemoramide, thebacon or trimeperidine, or suitable salts thereof.

Other addicting agents are, for example, barbiturates, such as allobarbital, amylbarbital, butabarbital, hexobarbital, mephobarbital, metharbital, methohexital, pentobarbital, phenobarbital, phenethylbarbital, secobarbital, talbutal or thiopental; as well as glutethimide, methaqualone, chloral or alcohol.

The 4-amino-3-p-halophenylbutyric acids, or said derivatives, correspond to the formula

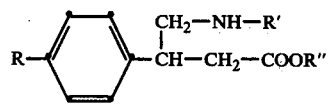

wherein R is halo, e.g. fluoro, chloro or bromo, or the pseudohalogen trifluoromethyl, R' is hydrogen, lower alkanoyl or phenyl-lower alkanoyl, e.g. acetyl, propionyl, butyryl, benzoyl or phenylacetyl, and R" is hydrogen, lower alkyl or phenyl-lower alkyl, e.g. methyl, ethyl, propyl, butyl or benzyl, as well as salts said acids or esters with therapeutically acceptable acids or bases.

The analgesically effective amounts of said narcotics, i.e. the useful doses thereof, are well known in the art and the analgesically non-enhancing amounts of said 4-amino-3-p-halophenylbutyric acids, or said derivatives thereof, can easily be determined in classical tests, e.g. those illustrated by said Vol. 54 of Brit. J. Pharmacol. In general, such doses are advantageously between about 0.01 and 5 mg/kg/day, preferably between about 0.1 and 1 mg/kg/day, or a single dosage unit between about 1 and 10 mg/day.

The newly discovered activity of said 4-amino-3-p-halophenylbutyric acids and their derivatives can be demonstrated in relevant tests, using preferably mammals, e.g. rodents, as test objects. Thus, for example, baclofen, a representative member of said aminoacids, causes at p.o. doses down to about 2.5 mg/kg/day an impressive, dose-related reduction in both qualitative and quantitative measures of mouse jumping. (Arch. int. Pharmacodyn. 190, p. 213, 1971). In this test, mice are injected subcutaneously with 20 mg/kg morphine sulfate, in form of an about 0.2% aqueous solution, seven times over a 2-day period. Two hours after the last dose a similar solution of 100 mg/kg naloxone is injected intraperitoneally, which causes all mice to jump. In addition to a quantal measure, the total of individual jumping episodes is recorded and the influence of test substances on this behavior is determined by administering them one hour prior to the naloxone challenge. In separate tests other muscle relaxants, e.g. methocarbimol, fail to cause jumping protection at p.o. doses as high as 600 mg/kg/day, indicating that the effect of baclofen is not due to its muscle relaxant action. Similarly, p.o. doses, down to about 2.5 mg/kg/day, of baclofen markedly attenuate the aberrant behavior induced by naloxone challenge of heavily morphine sulfate dosed rats (10 × 38.75 mg/kg/2.5 days). Similarly, subcutaneous doses down to 1 mg/kg/day of baclofen markedly attenuated the abstinence syndrome of morphine addicted rhesus monkeys, which were already in withdrawal by withholding the normal maintenance doses of morphine. This was again accomplished without any signs of muscle relaxation due to baclofen and was therefore below the muscle relaxant dose of baclofen in this species.

In another test suitably trained rats have an opportunity to intravenously inject themselves with morphine by pressing a lever activating the delivery-mechanism for aqueous morphine sulfate via an indwelling cannula. Presumably the injection is perceived pleasurable, rats soon become addicted and, on deprivation, extreme withdrawal symptoms are manifested. Baclofen, at p.o. doses al low as 1.25 mg/kg/day during 5 day periods, causes a distinct reduction in the amount of self-administered morphine sulfate, as well as a suppression of withdrawal symptoms in addicted animals, hitherto only achieved by administration of a morphine substitute, such as methadone.

The new method for reducing the addiction liability of narcotics, or their withdrawal effects, comprises preferably the enteral, e.g. oral or anal administration of said compositions, advantageously in the form of a single dosage unit three times per day. Also parenteral, e.g. intramuscular or intravenous, administration may be chosen, or mixed regimens, e.g. intravenous administration of any known narcotic composition, followed by the oral administration of a spasmolytically ineffective amount of any known composition of said 4-amino-3-p-halophenylbutyric acids or their derivatives, e.g. LIORESAL ®.

The pharmaceutical excipient, mentioned under item (C) is preferably such for enteral administration, e.g. for tablets, capsules or suppositories, comprising the active ingredients together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously solidified fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively, and contain about 1 to 90%, preferably about 2 to 50% of the active ingredient by weight.

The following examples are intended to illustrate the invention and are not to be construed as being limitations thereon.

EXAMPLE 1

Preparation of 1,000 tablets each containing 2.5 mg of the active ingredients:

| Formula: | |
| --- | --- |
| Levorphanol tartrate | 2.5 g |
| Baclofen | 2.5 g |
| Lactose | 115.7 g |
| Corn starch | 7.5 g |
| Polyethylene glycol 6000 | 7.5 g |
| Talcum powder | 7.5 g |
| Magnesium stearate | 1.8 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

In the analogous manner tablets are prepared, containing instead of levorphanol tartrate either 2.5 mg of methadone hydrochloride or 5 mg of oxycodone hydrochloride.

EXAMPLE 2

Preparation of 1,000 chewable tablets each containing 30 and 2.5 mg. of the active ingredients:

| Formula: | |
| --- | --- |
| Codeine phosphate | 30.0 g |
| Baclofen | 2.5 g |
| Mannitol | 267.0 g |
| Lactose | 179.5 g |
| Talcum | 20.0 g |
| Glycine | 10.0 g |
| Stearic acid | 10.0 g |
| Saccharin | 1.0 g |
| 5% Aqueous gelatin solution | q.s. |

Procedure:

All the powders are passed through a screen with 0.25 mm openings. The mannitol and lactose are blended, granulated with the gelatin solution, the wet mass passed through a screen with 2 mm openings, dried at 50° and passed through a screen with 1.7 mm openings. The drug substance, glycine and saccharin are throughly blended, the mannitol-lactose granulation, stearic acid and talcum added, the whole mixed until homogeneous and compressed into tablets using concave punches with 10.3 mm diameter, uppers bisected.

Analogously prepared tablets contain 50 mg of pentazocine lactate or 50 mg of meperidine hydrochloride instead of the codeine phosphate.

EXAMPLE 3

Preparation of 1,000 tablets each containing 100 and 5 mg of the active ingredients:

| Formula: | |
|---|---|
| Meperidine hydrochloride | 100.0 g |
| Baclofen | 5.0 g |
| Lactose | 248.5 g |
| Corn starch | 12.5 g |
| Polyethylene glycol 6000 | 15.0 g |
| Talcum powder | 15.0 g |
| Magnesium stearate | 4.0 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets using concave punches with 10.3 mm diameter, uppers bisected.

EXAMPLE 4

Preparation of an intramuscular solution containing 10 mg and 5 mg of the active ingredients per vial.

| Formula: | |
|---|---|
| Morphine sulfate | 85.0 g |
| Baclofen | 42.5 g |
| Chlorobutanol | 85.0 g |
| Methylcellulose 100 cps. | 178.5 g |
| Polysorbate 80 | 85.0 g |
| Sodium chloride | 136.0 g |
| Sodium carboxymethylcellulose 70 | 51.0 g |
| Water for injection | 17 lt |

Procedure:

The chlorobutanol is dissolved in 12 lt of water at 90° while stirring, followed by sodium carboxymethylcellulose and methylcellulose. After dissolution agitation is continued for 15 minutes, the solution cooled to 10° for 12 hours and the polysorbate is added. Morphine sulfate, baclofen and sodium chloride are dissolved in 500 ml of water each, if necessary with warming. All solutions are combined, the volume of the solution is made up to 17 lt with water and the whole is filtered through a sintered glass filter. The filtrate is steam sterilized in 2 lt bottles at 100° for 3 hours and 15 minutes and the contents filled into 2 ml sterile vials.

Analogously a solution is prepared, containing 50 mg meperidine hydrochloride instead of the morphine sulfate, per vial.

We claim:

1. A method for reducing either the addiction liability of an addicting agent, or the withdrawal symptoms caused by it, which consists in administering to a mammal in need of said agent, or suffering from withdrawal symptoms caused by the lack of it, enterally or parenterally a composition comprising: (A) an addicting amount of a member selected from the group consisting of a barbiturate and a narcotic agent, (B) a compound of the formula

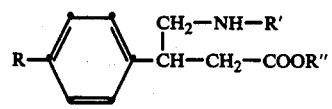

wherein R is fluoro, chloro, bromo or the pseudohalogen trifluoromethyl, R' is hydrogen, lower alkanoyl or phenyl-lower alkanoyl, and R" is hydrogen, lower alkyl or phenyl-lower alkyl, or a salt of said acids or esters with therapeutically acceptable acids or bases, in an effective but non-muscle relaxing amount of between about 0.1 and 1 mg/kg/day and (C) a pharmaceutical excipient.

2. A method as claimed in claim 1, wherein the narcotic agent is a member selected from the group consisting of alphaprodine, anileridine, bezitramide, codeine, dihydrocodeine, diphenoxylate, ethylmorphine, fentanyl, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine, and a therapeutically acceptable salt thereof.

3. A method as claimed in claim 1, wherein the narcotic agent is a member selected from the group consisting of acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, codeine methylbromide, codeine-N-oxide, cyprenorphine, desomorphine, dextromoramide, dextrorphan, diampromide, diethylthiambutene, dihydromorphine, dimenoxadol, dimepheptanol, dimethylthiamubutene, dioxaphetyl butyrate, dipipanone, drotebanol, ethylmethylthiambutene, etonitazene, etorphine, etoxeridine, furethidine, heroin, hydromorphinol, hydroxypethidine, ketobemidone, levomoramide, levophenacylmorphan, methyldesorphine, methyldihydromorphine, morpheridine, morphine methylbromide, morphine methylsulfonate, morphine-N-oxide, myrophin, nicocodeine, nicomorphine, noracymethadol, norlevorphanol, normethadone, normorphine, norpipanone, phenadoxone, phenampromide, phenomorphan, phenoperidine, piritramide, pholcodine, proheptazine, properidine, propiram, racemoramide, thebacon, trimeperidine, and a therapeutically acceptable salt thereof.

4. A method as claimed in claim 1, wherein the narcotic agent is a member selected from the group consisting of codeine phosphate, levorphanol tartrate, meperidine hydrochloride, methadone hydrochloride, morphine sulfate, oxycodone hydrochloride and pentazocine lactate.

5. A method as claimed in claim 1, wherein the barbiturate is a member selected from the group consisting of allobarbital, amylbarbital, butabarbital, hexobarbital, mephobarbital, metharbital, methohexital, pentobarbital, phenobarbital, phenethylbarbital, secobarbital, talbutal, thiopental, and a therapeutically acceptable salt thereof.

6. A method as claimed in claim 1, wherein the 4-amino-3-p-halophenylbutyric acid compound is baclofen.

7. A method as claimed in claim 6, wherein the dosage unit contains between about 1 and 10 mg of baclofen.

* * * * *